United States Patent [19]
Zemel et al.

[11] Patent Number: 5,463,899
[45] Date of Patent: Nov. 7, 1995

[54] SIMULTANEOUS MEASUREMENT OF GAS THERMAL CONDUCTIVITY AND MASS FLOW

[75] Inventors: Jay N. Zemel, Jenkintown; Hsin-Yi Hsieh, Drexel Hill, both of Pa.

[73] Assignee: Gas Research Institute, Chicago, Ill.

[21] Appl. No.: 290,026

[22] Filed: Aug. 12, 1994

[51] Int. Cl.[6] ................................................ G01F 1/68
[52] U.S. Cl. .................. 73/195; 73/202.5; 73/204.23; 73/204.25
[58] Field of Search ..................... 73/195, 202.7, 73/202.5, 204.23, 204.25

[56] References Cited

U.S. PATENT DOCUMENTS

| | | |
|---|---|---|
| 3,425,277 | 2/1969 | Adams . |
| 3,519,924 | 7/1970 | Burton . |
| 3,972,681 | 8/1976 | Clack et al. ........................... 23/253 R |
| 4,319,483 | 3/1982 | Durham, Jr. et al. ................ 73/204.25 |
| 4,332,157 | 6/1982 | Zemel et al. .................................. 73/26 |
| 4,449,401 | 5/1984 | Kaiser et al. . |
| 4,453,405 | 6/1984 | Zemel . |
| 4,463,601 | 8/1984 | Rask . |
| 4,608,865 | 9/1986 | Muller et al. . |
| 4,850,714 | 7/1989 | Wiegleb . |
| 4,916,948 | 4/1990 | Inada et al. . |
| 5,303,584 | 4/1994 | Ogasawara et al. ................. 73/204.21 |

Primary Examiner—Richard Chilcot
Assistant Examiner—Jewel V. Artis
Attorney, Agent, or Firm—Speckman, Pauley & Fejer

[57] ABSTRACT

A system and method for simultaneous measurement of thermal conductivity and the mass flow of a fluid comprising two conduits arranged in a concentric or bypass arrangement through which the fluid is flowing, a pyroelectric anemometer disposed within each of the two conduits, and a differential amplifier connected to each of the pyroelectric anemometers which generate a signal based upon flow of fluid through the conduits.

11 Claims, 3 Drawing Sheets

SIMULTANEOUS MEASUREMENT OF GAS THERMAL CONDUCTIVITY AND MASS FLOW

BACKGROUND OF THE INVENTION

1. Field of the Invention

This invention relates to a system and method for simultaneous measurement of thermal conductivity and mass flow of a fluid using pyroelectric anemometers. The system and method of this invention are based upon the electrical response characteristics of pyroelectric anemometers to fluid flow.

2. Description of Prior Art

Thermal flow meters utilize the convective heat transfer between a moving fluid stream and a heated solid to measure flow rate. Thermal energy is transferred from the heated solid to the flowing fluid resulting in a decrease in the temperature of the heated solid, which decrease can be used as an indicator of flow rate. A thermal flow meter has two basic components: a heater and a transducer. The heater is used to elevate the solid temperature and the transducer detects the flow-induced change of the thermal process. The transducer converts the change of temperature or heat loss into an electronic signal that can be processed by electronic instruments. Thermal flow sensors are utilized in, for example, meteorology to determine wind velocity and direction, indoor climate control, biomedical measurements, such as respiration and blood flow, transport and process industries, and fluid dynamics research, such as wind-tunnel experimentation.

A pyroelectric anemometer is a device for measuring fluid flow comprising suitably oriented pyroelectric materials on which are deposited measuring electrodes symmetrically disposed about a deposited heater element. The pyroelectric materials have a high thermal sensitivity. The heater element is driven by an alternating current which generates an alternating thermal current at twice the current frequency. This alternating thermal current, in turn, generates an alternating voltage output at the thermal excitation frequency which depends on the velocity of the fluid flow. Upstream and downstream electrodes disposed on a pyroelectric material substrate measure the alternating charge redistribution of the pyroelectric substrate material due to the alternating heat flowing from the centrally located heating element on the substrate. When a fluid flow is present over the pyroelectric material substrate, the upstream electrode is cooled to a greater extent than the downstream electrode and, thus, its temperature is lower and, thus, the charge redistribution associated with the upstream electrode is less than the charge redistribution associated with the downstream electrode. The electrodes are connected to a differential amplifier whose output is connected to a further amplifier and an electronic meter. Means for heating the pyroelectric material substrate in a fluctuating manner to permit the necessary charge redistribution are also provided. As the temperature of the heater varies, the output of the two electrodes varies and, in addition, the amplitude and phase (relative to the input thermal signal) of their outputs is affected, depending upon whether they are upstream or downstream of the heating element when the fluid flows. The extent of the difference in the signal from the two electrodes is indicative of the flow velocity. A pyroelectric anemometer suitable for use in the system and method of this invention is taught by U.S. Pat. No. 4,332,157.

Pyroelectric anemometers have been shown to have extraordinarily high precision over a broad range of flows, particularly when compared to calorimetric type thermal flow meters such as capillary flow meters, and boundary-layer type thermal flow meters, such as hot wire/film anemometers and silicon flow meters.

U.S. Pat. No. 4,850,714 teaches an apparatus for measuring thermal conductivity of a gas using two temperature-dependent measuring resistors disposed along a bypass-type gas flow path. More particularly, the '714 patent teaches locating a second heatable and temperature-dependent measuring resistor in close proximity to a first measuring resistor, one behind the other along the gas flow path, and locating these two measuring resistors electrically in opposite arms of a measuring bridge.

An electrical thermal flow meter comprising a pair of thermistors in opposite arms of a Wheatstone bridge and an electric heater positioned in heat transfer relation with respect to the first thermistor and isolated from the second thermistor is taught by U.S. Pat. No. 3,425,277. Flowmeters are also taught by U.S. Pat. No. 4,449,401 which teaches a flow meter having a Venturi tube position within a passage that receives a portion of the airflow in the throat of which is disposed a constant temperature thermal anemometer which generates an output signal as a function of the total mass airflow through the flow meter; U.S. Pat. No. 4,916,948 which teaches thermal sensitive resistors positioned within a housing, externally and internally with respect to a pipe passage disposed within a central portion of the housing so that an accurate flow rate can be measured even when the fluid flow rate varies within a single plane; and U.S. Pat. No. 4,463,601 which teaches an airflow sensor for determining mass flow rate in a branch of a system having two flow branches which meet at a junction. However, none of the methods and apparatuses taught by these references is capable of simultaneously measuring thermal conductivity and mass flow rate of a gas.

U.S. Pat. No. 4,453,405 teaches a pyroelectric vorticimeter which is used to measure shear flow components in both the X and Y directions where the two shear flow components are electrically multiplied to provide an electronic indication of the vorticity of flow in a region of the pyroelectric substrate. A fluctuating heat input is applied to the pyroelectric substrate and two spaced conductor elements are used to sense a difference in surface charge fluctuations between the two conductor elements.

U.S. Pat. No. 4,608,865 teaches an integrated circuit pyroelectric sensor which uses two pyroelectric compositors for measuring a differential voltage across gates. The voltage and charge stored across each pyroelectric compositor is a function of temperature.

Finally, U.S. Pat. No. 3,519,924 teaches a heat-sensitive frequency-selective apparatus for measuring variable conditions of flowing fluid, such as temperature characteristics. The crystal unit is used to sense fluid velocity as a function of temperature difference sensed by the crystal unit, given a constant direction of flow and a constant density of the fluid.

None of the prior art of which we are aware teaches the use of a thermal mass flow meter for simultaneous measurement of thermal conductivity and mass flow.

SUMMARY OF THE INVENTION

It is an object of this invention to provide a method for simultaneous measurement of thermal conductivity and mass flow of a fluid.

It is another object of this invention to provide a system for simultaneous measurement of thermal conductivity and mass flow of a fluid.

These and other objects are achieved by a system for simultaneous measurement of thermal conductivity and mass flow of a fluid comprising flow division means for forming two parallel flowing streams of the fluid being measured, thermal mass flow meter means for measuring the velocity of the fluid in each of the two parallel flowing streams, the thermal mass flow meter means being disposed within the two parallel flowing streams, and signal receiving means for receiving a signal from the thermal mass flow meter means.

More particularly, the system of this invention comprises two conduits arranged in one of a concentric conduit arrangement wherein one of the conduits is disposed concentrically within the other conduit and a bypass conduit arrangement wherein the ends of one of the conduits are in communication with the other of the conduits. The velocity of the fluid flowing through the two conduits in either arrangement of said conduits is measured by a pyroelectric anemometer disposed in each of the two conduits. Each pyroelectric anemometer, in turn, is connected to a signal receiving means, preferably in the form of a differential amplifier, for measuring the signal generated by the pyroelectric anemometer as a result of the fluid flowing through the respective circular conduit.

The method for simultaneously measuring the thermal conductivity and mass flow of a fluid in accordance with one embodiment of this invention comprises passing the fluid to be measured through two conduits arranged in a concentric or bypass arrangement, inserting a linear pyroelectric anemometer into the interior of each conduit, simultaneously detecting a differential signal from each of the linear pyroelectric anemometers, and calculating the thermal conductivity and mass flow of the fluid from the differential signals.

BRIEF DESCRIPTION OF THE DRAWINGS

These and other objects and features of this invention will be better understood from the following detailed description taken in conjunction with the drawings, wherein.

DESCRIPTION OF PREFERRED EMBODIMENTS

Pyroelectricity is the electricity generated by temperature change on certain crystals due to spontaneous polarization of the crystals which creates surface charges on certain surfaces thereof. The surface charges are eventually neutralized by free electric charges acquired from surrounding media and from the conduction current in the pyroelectric crystal. If the temperature of the pyroelectric crystal changes, for example by heating, surface charges which can be detected by conventional electronic instruments are induced by the change of spontaneous polarization.

Figure 3:
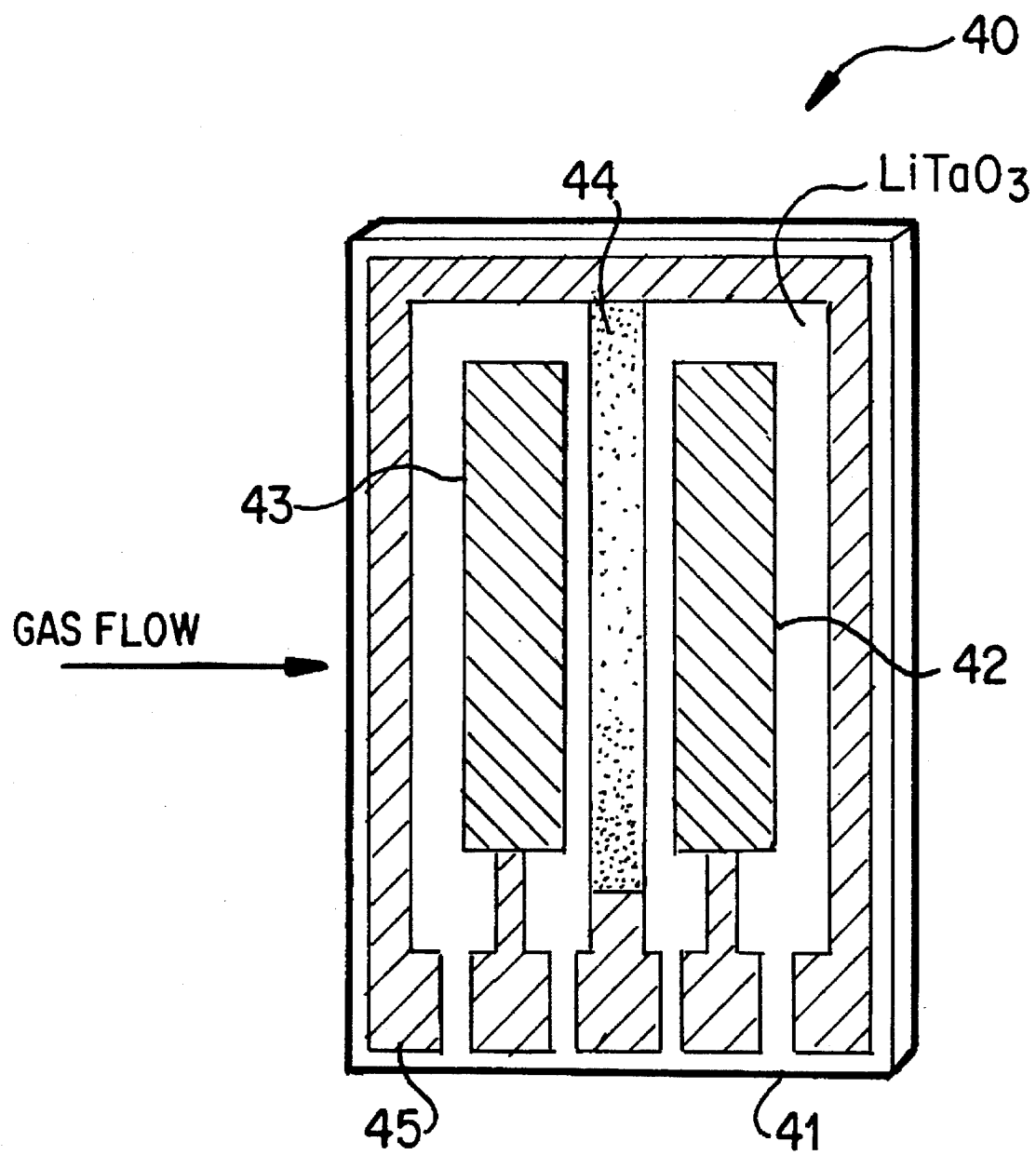
FIG. 3 is a diagram of a typical linear pyroelectric anemometer suitable for use in the system and method of this invention.

A pyroelectric anemometer is a thermal mass flow meter that uses pyroelectric material, that is crystals, as the temperature transducer. FIG. 3 shows a typical linear pyroelectric anemometer 40 suitable for use in the system and method of this invention. Pyroelectric anemometer 40 comprises a pyroelectric material substrate 41, preferably a small z-cut $LiTaO_3$ chip. $LiTaO_3$ is preferred for its high pyroelectric co-efficient ($1.9 \times 10^{-8}$ coulomb/$cm^2$°K.) and high Curie temperature (609° C.). The front surface of the substrate 41 has a thin center heater NiCr film strip 44 positioned at its center and two electrode NiCr film strips 42, 43 deposited symmetrically beside center heater NiCr film strip 44. The back of substrate 41 has a thin film of NiCr deposited on it as the ground. Each of electrode NiCr film strips 42, 43 and center heater NiCr film strip 44 are electrically connected to substrate 41 by conducting pad 45 formed of a conductive metal, for example, gold.

Accordingly, electrode NiCr film strips 42, 43 with pyroelectric material substrate 41 sandwiched between them and the ground are, in fact, capacitors. The charges collected on the electrodes depend on the change of the temperature and applied field.

The operating principles of pyroelectric anemometer 40 are as follows. Center heater NiCr film strip 44 is driven by an ac current I with a frequency f at a few Hz as follows:

$$I = I_o \cos(2\pi f t)$$

where $I_o$ is the amplitude of the electric current and t is the time. Sinusoidal heating is required because any charges created by constant heating would be neutralized by the leakage current. The power $P_h$ generated by the electric current I is:

$$P_h = IR_h \tfrac{1}{2} I_o^2 R_h [1 + \cos(4\pi f t)]$$

where $R_h$ is the resistance of the NiCr strips. The power generated has two components: a dc component with magnitude $\tfrac{1}{2}I_o^2 R_h$, and an ac component having the amplitude $\tfrac{1}{2}I_o^2 R_h$. The frequency of the ac power is double the frequency of the electric current. The dc power induces a constant surface charge that is neutralized by the leakage current. The ac power creates an oscillating temperature field that propagates into the pyroelectric anemometer with an angular frequency $\omega = 4\pi f$. The oscillating temperature under the electrode induces oscillating charges and a corresponding oscillating current on the electrode due to the pyroelectric effect. The difference between the pyroelectric current induced on the two electrodes, $\Delta i$, is used to measure the flow rate according to the following equation:

$$\Delta i = \bar{p} A_e \frac{d}{dt} [<\theta>_D - <\theta>_U]$$

where $\bar{p}$ is the pyroelectric co-efficient, $A_e$ is the electrode area, $<\theta>$ is the temperature of the pyroelectric crystal averaged under the electrode, and U and D denote the upstream and downstream electrodes, respectively. At zero fluid flow, both electrodes 42, 43 will have the same oscillating current due to symmetry and $\Delta i$ will equal zero. As fluid flows, the convective heat loss at the upstream electrode will be different from the downstream electrode, inducing a different pyroelectric current on the two electrodes such that $\Delta i$ is no longer equal to zero.

Accordingly, it is apparent that the orientation of pyroelectric anemometer 40 within the fluid stream is critical for obtaining the desired results. In particular, center heater NiCr film strip 44 must be disposed perpendicular to the direction of flow of the gas being measured. In addition, one of electrode NiCr film strips 42, 43 must be disposed upstream of the other relative to the direction of fluid flow.

We have determined that the basic relation for the response of a linear pyroelectric anemometer to the flow of fluid in a conduit, that is the differential signal obtained from the linear pyroelectric anemometer, obeys a general law of the form:

Amplitude =

$$\kappa_{gas} \left\{ \cfrac{1}{\cfrac{1}{A\sqrt{Re}} + \cfrac{1}{B*Re}} \right\} = \cfrac{\kappa_{gas} ABRe^{3/2}}{A\sqrt{Re} + B*Re}$$

where A and B are material parameters of the pyroelectric material and the fluid.

Figure 1:
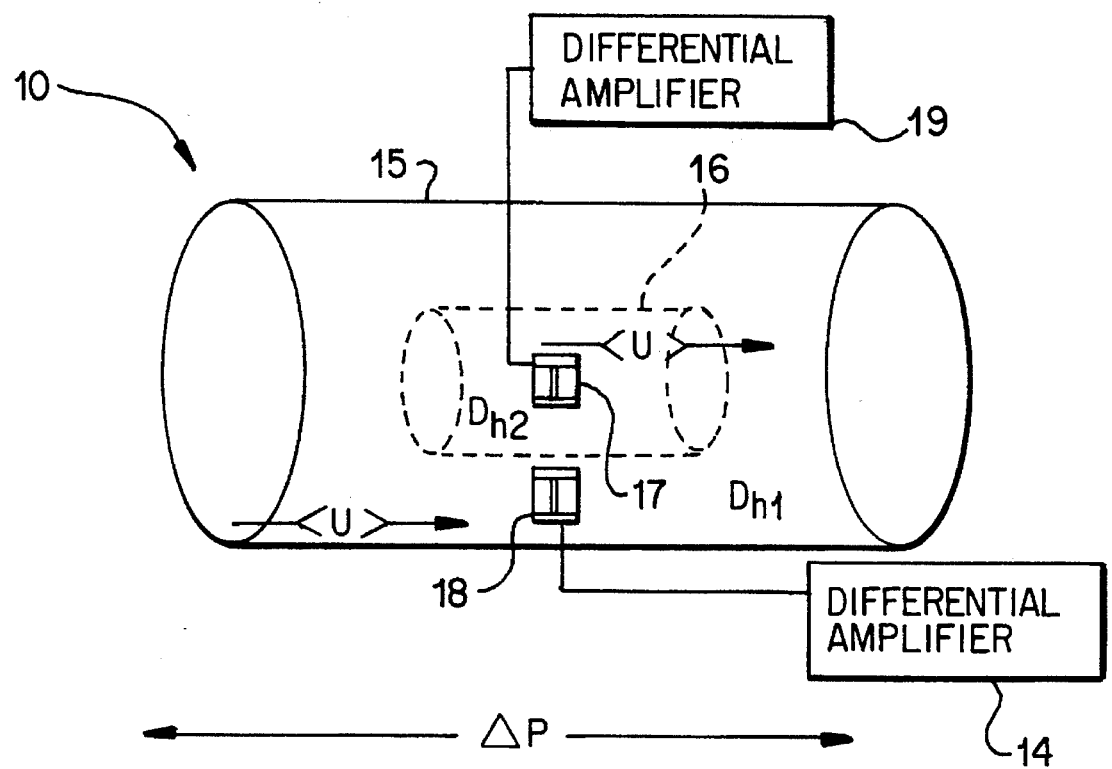
FIG. 1 is a schematic diagram of a system for simultaneous measurement of thermal conductivity and mass flow of a fluid flowing through a concentric arrangement of circular conduits in accordance with one embodiment of this invention.
Figure 2:
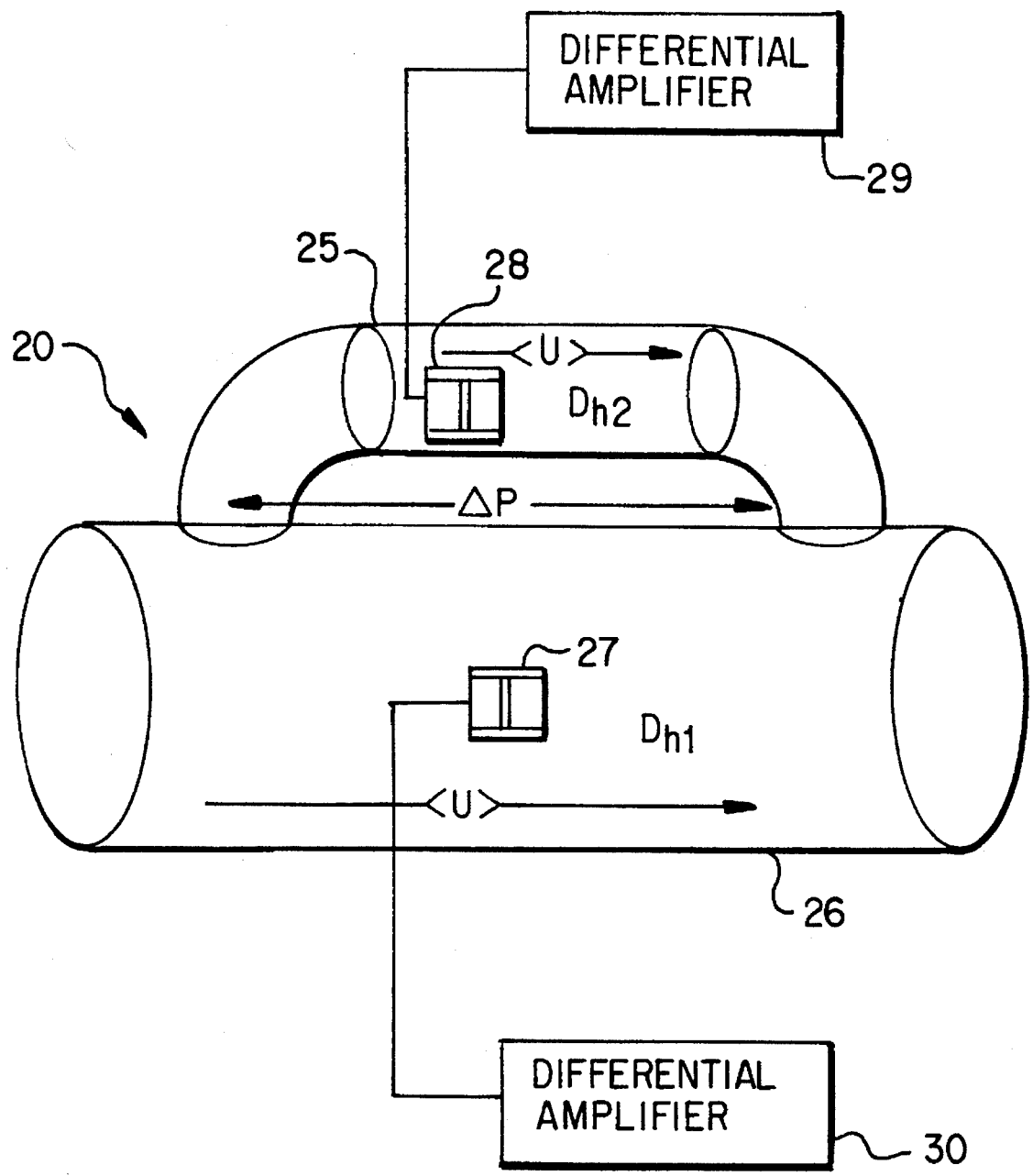
FIG. 2 is a schematic diagram of a system for simultaneous measurement of thermal conductivity and mass flow of a fluid flowing through a bypass arrangement of circular conduits in accordance with another embodiment of this invention.

The underlying concept of the system and method of this invention is based on the fact that, on average, the velocity in two concentric or bypass conduits is different in accordance with FIGS. 1 and 2. FIG. 1 shows a concentric arrangement of circular conduits suitable for use in the system and method of this invention in which circular conduit 16 is concentrically disposed within circular conduit 15. Disposed within each of circular conduits 15 and 16 is a pyroelectric anemometer 18 and 17, respectively, each of which is connected to a differential amplifier 14, 19 for receiving the signals generated by pyroelectric anemometers 18, 17 from which the thermal conductivity and mass flow of the fluid flowing through concentric conduits 15, 16 can be determined.

Similarly, FIG. 2 shows bypass arrangement 20 for simultaneous measurement of thermal conductivity and mass flow of a fluid flowing therethrough comprising main circular conduit 26 in which is disposed main conduit pyroelectric anemometer 27, and bypass circular conduit 25, the ends of which are in communication with main circular conduit 26, in which is disposed bypass conduit pyroelectric anemometer 28. As in concentric system 10 shown in FIG. 1, each of main conduit pyroelectric anemometer 27 and bypass conduit pyroelectric anemometer 28 is connected to a differential amplifier 30, 29, respectively, for receiving the signals generated by main conduit pyroelectric anemometer 27 and bypass conduit pyroelectric anemometer 28 as a result of fluid flowing through bypass system 20.

It will be apparent to those skilled in the art that conduits 15, 16, although depicted as being circular for purposes of illustrations, are not limited in any way to having a circular cross-sectional area. Conduits having square, rectangular or polygonal cross-sectional areas may be utilized in the system and process of this invention.

Referring to FIGS. 1 and 2, the Reynolds number for the flow of fluid through a circular conduit is defined as:

$$Re = \cfrac{U \cdot D_h}{v}$$

where U is the average velocity in the circular conduit, $D_h$ is the hydraulic diameter of the conduit defined as the ratio of four times the area of the conduit divided by its wetted perimeter, and $v$ is the kinematic viscosity of the fluid.

As shown in FIG. 1, the system for simultaneous measurement of thermal conductivity and mass flow of a fluid, for example a gas, in accordance with one embodiment of this invention comprises two concentric circular conduits 15, 16 with hydraulic diameters $D_{h1}$ and $D_{h2}$, respectively. The average velocity of the fluid flowing in the two circular conduits is proportional to $D_h^2$. Accordingly, if $D_{h2}$ is less than $D_{h1}$, then the Reynolds number in circular conduit 16 must also be less than the Reynolds number in circular conduit 15. This relationship is the key to the system of this invention and applies both to the concentric arrangement 10 shown in FIG. 1 as well as the bypass arrangement 20 shown in FIG. 2. Accordingly, in the two circular conduits 16, 15, the corresponding Reynolds numbers are:

$$Re_1 = \cfrac{U_1 \cdot D_{h1}}{v}$$

$$Re_2 = \cfrac{U_2 \cdot D_{h2}}{v}$$

If the Reynolds number of circular conduit 16 is small enough, the amplitude, that is the simultaneous signals from pyroelectric anemometers 18 and 17 in circular conduits 15 and 16, respectively, varies as follows:

$$\text{Amplitude}_1 = I_1 = \kappa_{gas} A \cdot Re_1$$

$$\text{Amplitude}_2 = I_2 = \kappa_{gas} B \cdot \sqrt{Re_2}$$

Under these conditions, $$I_2^2 = \kappa_{gas}^2 B^2 Re_2 = \kappa_{gas}^2 B^2 \cfrac{U_2 \cdot D_{h2}}{v_{gas}}$$

and $$I_1 = \kappa_{gas} A \cdot Re_1 = \kappa_{gas} A \cdot \cfrac{U_1 \cdot D_{h1}}{v_{gas}}$$

where I uses the definitions of the Reynolds numbers recited hereinabove. If we ratio these quantities, we obtain $$\cfrac{I_2^2}{I_1} = \cfrac{\kappa_{gas}^2 B^2 \cfrac{U_2 \cdot D_{h2}}{v_{gas}}}{\kappa_{gas} A \cdot \cfrac{U_1 \cdot D_{h1}}{v_{gas}}} = \kappa_{gas} \cfrac{B^2 \cdot D_{h2}^3}{A \cdot D_{h1}^3}$$

Because A, B, $D_{h1}$ and $D_{h2}$ are all measurable, A and B being constant for different gases, we obtain the thermal conductivity, $\kappa_{gas}$. Once $\kappa_{gas}$ is known, the effected velocity of the gas and the Reynolds number for the system can be determined.

The benefit of this device is that it provides additional information on the composition of the gas in real time. Thermal conductance measurements are often used in gas chromatography, though not in a clear quantitative fashion. By measuring the thermal conductivity, the user has a type of chemical sensor that can alert the user to variations occurring in the gas stream.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A system for simultaneous measurement of thermal conductivity and mass flow of a fluid comprising:
   flow division means for forming two parallel flowing streams of said fluid;
   thermal mass flow meter means for measuring the velocity of said fluid in each of said two parallel flowing streams, said thermal mass flow meter means disposed within said two parallel flowing streams; and
   signal receiving means for receiving a signal from said thermal mass flow meter means.

2. A system in accordance with claim 1, wherein said flow division means comprises two conduits having different internal diameters, said two conduits arranged in one of a concentric arrangement and a bypass arrangement.

3. A system in accordance with claim 2, wherein said thermal mass flow meter means comprises a pyroelectric anemometer disposed in each of said two conduits.

4. A system in accordance with claim 3, wherein each of said pyroelectric anemometers is a linear flow measurement anemometer, said each of said pyroelectric anemometers comprising a heater element disposed perpendicular to the direction of flow of said flowing streams and an electrode on each side of said heater element, one of said electrodes disposed upstream of the other relative to the direction of flow of said flowing streams.

5. A system in accordance with claim 3, wherein said signal receiving means comprises a differential amplifier.

6. A system in accordance with claim 2, wherein said conduits have a circular cross-sectional area.

7. A system in accordance with claim 1, wherein said fluid is a gas.

8. A method for simultaneously measuring the thermal conductivity and the mass flow of a fluid comprising:
   passing a fluid through an arrangement of conduits selected from the group consisting of a concentric arrangement and a bypass arrangement, said concentric arrangement comprising two concentrically disposed conduits having different diameters, one disposed within the other, and said bypass arrangement comprising two substantially parallel conduits, the ends of one of said two conduits in communication with the other conduit of said two conduits;
   inserting a linear pyroelectric anemometer with a heater element disposed perpendicular to the direction of flow of said fluid into the interior of each of said conduits;
   simultaneously detecting a differential signal from each of said linear pyroelectric anemometers; and
   calculating the thermal conductivity and mass flow of said fluid from said differential signals.

9. A method in accordance with claim 8, wherein the differential signals from each of said linear pyroelectric anemometers is of the form:

Amplitude =

$$\kappa_{gas} \left\{ \frac{1}{\frac{1}{A\sqrt{Re}} + \frac{1}{B*Re}} \right\} = \frac{\kappa_{gas} A B Re^{3/2}}{A\sqrt{Re} + B*Re}$$

where
   $\kappa$ is the thermal conductivity;
   Re is the Reynolds number; and
   A and B are constants.

10. A method in accordance with claim 8, wherein said fluid is a gas.

11. A method in accordance with claim 8, wherein said conduits have a circular cross-sectional area.

* * * * *